United States Patent [19]

Reunanen

[11] 3,981,981

[45] Sept. 21, 1976

[54] METHOD OF RADIOIMMUNOASSAY EMPLOYING DIFFUSION

[76] Inventor: Matti Antero Reunanen, Kupittaankatu 11-13 C 38, 20520 Turku 52, Finland

[22] Filed: Jan. 18, 1974

[21] Appl. No.: 434,733

[30] Foreign Application Priority Data
Jan. 25, 1973  Finland .................................. 202/73

[52] U.S. Cl. ................................. 424/1.5; 23/230 B
[51] Int. Cl.² ..................... G01N 33/00; G21H 5/02
[58] Field of Search ................ 250/303, 304; 424/1, 424/1.5, 12; 23/230 B

[56] References Cited
OTHER PUBLICATIONS

Kabat, Structural Concepts in Immunology and Immunochemistry, Holt, Reinhart and Winston, Inc., New York, 1968, pp. 67–81.

*Primary Examiner*—Benjamin R. Padgett
*Assistant Examiner*—Christine M. Nucker
*Attorney, Agent, or Firm*—Sughrue, Rothwell, Mion, Zinn and Macpeak

[57] ABSTRACT

A method for the radioimmunoassay of small molecules consisting of bringing the large-molecule antibody of the small-molecule antigen to be determined into a slit-shaped chamber between dialysis membranes in a reaction vessel, bringing the antigen to be determined into this tank, into which a specified quantity of the radioactive form of this antigen has been added. During incubation the antigen and its radioactive form freely penetrate through the membranes and react with the antibody, whereupon washing stage is accomplished. Water and the unreacted antigen freely pass through the membranes, and the radioactivity of the washed complex remaining between the membranes is measured and the antigen is determined from this quantitatively in a way known.

5 Claims, 4 Drawing Figures

METHOD OF RADIOIMMUNOASSAY EMPLOYING DIFFUSION

BACKGROUND OF THE INVENTION

The object of the present invention is a method for the radioimmunoassay of small molecules, such as peptide hormones.

In a radioimmunoassay (RIA) the quantity of a component is determined by adding to a sample the radioactive form of the same substance and the antibody of the substance to be studied. Hence, the component subject to investigation and the added radioactive substance react with the antibody, whereby the higher the proportion of the complex that is radioactive, the lower is the concentration of the studied substance in the sample. This results from the fact that so little of the antibody has been added that all of the substance to be studied and of its radioactive form (antigen) cannot react, for which reason the radioactive and the non-radioactive form compete with each other. By measuring the radioactivity of the complex or of the free form or of both, it is possible to calculate the quantity of the component to be studied in the sample.

The most difficult step of work in radioimmunoassays is the separation of the complex and the free antigen from each other with a sufficiently high precision by means of methods suitable for mass working. There are several techniques in use, depending on the antigen and the operator. A brief summary will be given of these methods of separation:

1. Electrophoresis requires a lot of active working contribution and the sample size is limited (maximum limit 200 $\mu$l).
2. Gel filtering requires a lot of active work and time.
3. Non-specific precipitation by means of protein precipitants also encloses free antigen inside the precipitate and requires several washing steps.
4. Immunoprecipitation comprises precipitating of the complex by means of an antibody of the antibody. The precipitate produced is difficult to handle carefully enough, i.e. it can be lost with the washing liquids.
5. By means of adsorption onto a solid phase it is possible to remove the unbound hormone out of the sample and to calculate the complex retained in the liquid phase.
6. The antibody in the solid phase is allowed to react with the antigen, and the free component is washed off.

Among the listed methods, the last two listed are becoming increasingly used. They, however, involve certain limitations. For example, in adsorption onto a solid phase the total protein content of the mixture is critical and must be standardized precisely. The methods also require 2 to 3 precise steps of dosage. Moreover, when hormone contents are measured when determining reasons for disturbed states of metabolism, it is often necessary to choose different separation methods for different hormones. There are no standard methods, and for this reason clinical-chemical laboratories must have high and wide-range specialist knowledge.

SUMMARY OF THE INVENTION

When radioimmunological methods become more common in routine use, it becomes more and more important to utilize a method that is simpler and that can be applied to as many hormones as possible. The present invention is intended to meet this need. The method in accordance with the present invention is simple for the operator and it is economical and flexible. Most of the work has been transferred to be done in long series at commercial companies, and only such steps which are absolutely necessary are carried out at the operating laboratories.

According to the method in accordance with the invention, the large-molecule antibody of the small-molecule antigen to be determined is placed in a narrow chamber formed between dialysis membranes in a reaction vessel in order to obtain rapid equilibrium, and a predetermined quantity of the radioactive form of the antigen, the sample and the non-radioactive form of the antigen are added into the reaction tank outside the dialysis bag. Incubation then takes place, and the antigen of the sample and the radioactive antigen freely pass through the membrane and partly react with the antibody thus forming a complex that does not pass through the membranes of the bag, and hereafter washing is carried out. The washing liquids are changed and the unreacted antigen freely passes through the membranes and is removed together with the washing liquids, whereby it is possible, by measuring the radioactivity of the complex remaining between the membranes, to determine the antigen-content of the sample in a way known.

According to the method in accordance with the invention, the antibody is pre-measured in dialysis bags, preferably as absorbed into some porous sheet-shaped material, and the radioactive antigen is pre-measured outside the bag, preferably on the bottom of the reaction vessel. The operator need only dose the patient's serum or plasma in the reaction vessel and to take the tanks into the reaction incubator and washing and calculation. Only the dosage of the plasma requires precision and individual handling of the samples, whereas the other steps are only transfer operations.

The invention will be described below in detail as being applied to peptide hormone determination. The method is, however, also suitable for the determination of other small-molecule substances, such as steroid hormones and drugs.

DESCRIPTION OF THE PREFERRED EMBODIMENT

Figure 1:
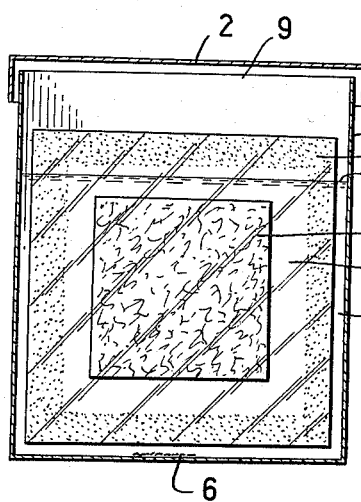
FIG. 1 shows the reaction vessel and dialysis bag as a longitudinal section and FIG. 2 as a cross section.
Figure 2:
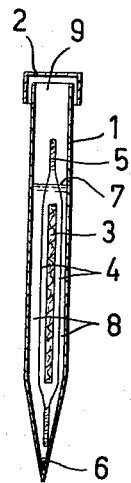
Figure 3:
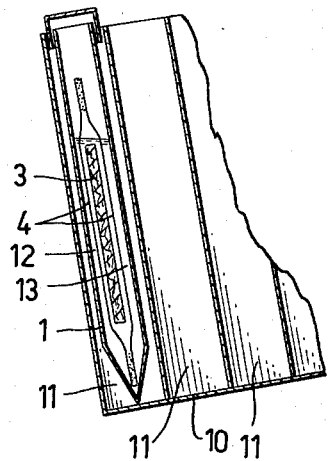
FIG. 3 shows the reaction vessel with its contents in a cassette at the incubation stage and FIG. 4 at the washing stage.
Figure 4:
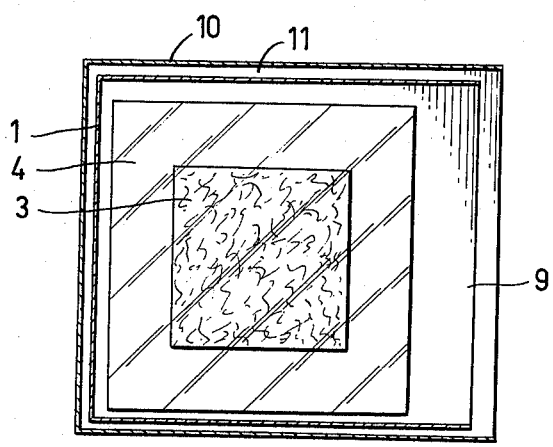

Referring now to the drawings in detail, the method works in peptide hormone determination as follows:

In the reaction vessel 1, in a space sealed by the cover 2, as absorbed in a porous sheet (e.g. cellulose acetate) 3 and dried, between dialysis membranes (e.g. of cellophane) 4 sealed by an adhesive seam 5, there is the antibody and on the bottom of the vessel 1 the radioactive form 6 of the antigen. The operator doses the plasma of the patient to be examined or a dilute of the plasma into the vessel 1 so that the liquid level 7 is above the top limit of the antibody sheet 3. Hence, liquid penetrates through the membranes 4 and the sheet 3 becomes wet. Since the hormone has a relatively small molecule size, it can pass through the membranes 4 to react with the antibody in the sheet 3, and in the liquid chamber 8 outside the dialysis bag the hormone content is reduced in proportion to the quantity of the hormone bound. At this incubation stage the reaction vessels 1 are with their mouths 9 upwards in the spaces 11 in the cassette 10, and the cassette is on a swaying base so that when the dialysis bag is moved by the force of gravitation to and fro in the vessel 1, liquid flows alternatingly from the chamber 12 into the chamber 13 and vice versa thus producing an efficient agitation in the liquid space 8 and a faster equilibrium. After completed incubation the cassette 10 with its contents is turned 90° so that the mouths 9 of the vessels 1 become directed towards the side, and water is introduced into the cassette container by pulsating so that the water alternatingly fills the vessels 1 and these are alternatingly emptied, an efficient rinsing being produced in this way. The free antigen adhered to the sheets 3 is also dialysed off the sheets, and the dialysis bags can be transferred to the counter.

The dialysis bags with their contents and the reaction vessel with their active hormones are preferably manufactured as one unit, so that the operator will only have to carry out the dosage of the patient's sample. For each species of hormone preferably a tank-bag combination of its own is used.

The following insulin determination is described as a second example of how the method is carried out in detail.

Commercial reagents are suitable or the reagents can be prepared in the laboratory. The antiserum containing the insulin antibody is obtained by immunizing Guinea pigs by several injections of pure insulin. As radioactive insulin, radio-iodinated insulin I-125 is used. Each reagent is closed in 25 µl of a buffer containing per liter of water: 40 mmoles phosphate buffer ($NaH_2PO_4$ and $Na_2HPO_4$), pH 7,4; 5 g cow plasma albumin; 30 mmoles EDTA; and 0,6 mmoles thiomersalate. For the assay three sets of vessels are required: vessels for the actual samples, control vessels and standard vessels.

To the sample vessel is introduced an antiserum dilution dosed on 15 × 15 mm cellulose acetate sheets (3) which after water evaporation are closed between Cellophane dialysis membranes (4). The appropriate dilution is determined in advance by means of an antiserum dilution series such that the dilution that takes up from 50 to 60 % of the radioactive insulin to be dosed. 20 pg of the above mentioned insulin I-125 is dosed to the bottom of the 25×20×2,5 mm reaction vessel (1).

The control vessels are made ready in the same manner except that instead of diluted serum from immunized Guinea pigs it was used serum from unimmunized Guinea pigs in the same dilution ratio and furthermore it is dosed to the bottom of the vessel (6) 100 µl of human serum out of which the insulin has been separated by absorbing to active charcoal. The standard vessels differ from the sample vessels in that it is dosed to them as to the control vessels 100 µl of human serum treated with active charcoal, and furthermore it is introduced to the bottom of vessel (6) non-radioactive insulin dosed according to the following geometric series: 0, 5, 10, 20, 40, 80, 160 and 320 pg.

All the above mentioned reagents are introduced to the vessels as dry and vessels are made ready in great members at a time.

By clinical determinations out of the prepared vessels two sample vessels, two control vessels and one standard series per patient are chosen. 100 µl serum from the patient is introduced to the sample vessels; 100 µl water is introduced to the control and standard series vessels; 900 µl of the above mentioned buffer containing additionally 9 g NaCl per liter is introduced to all the vessels.

Thereafter follows the steps of incubation and washing. The incubation time is 16 hours and the washing time 6 hours. Then, upon completion of the washing step, the radioactivity is counted by means of a gamma counter. The radioactivity of the control vessels shows a binding that is not specific and undependent upon the antibody, and it has to be substracted from all the results. A standard curve is drawn according the results of the standard series and from this curve the concentration of the samples can be obtained in known manner.

What I claim is:

1. A method of radioimmunoassay comprising the steps of:
    a. bringing the large-molecule antibody of the small-molecule antigen to be determined into a slit-shaped chamber between dialysis membranes in a reaction vessel,
    b. bringing the antigen to be determined into said vessel, into which a specified quantity of the radioactive form of this antigen has been added,
    c. incubating, whereby the antigen and its radioactive form freely penetrate through the membranes and react with the antibody,
    d. washing, whereby water and the unreacted antigen freely pass through the membranes, and
    e. measuring the radioactivity of the washed complex remaining between the membranes, and
    f. determining the antigen quantitatively.

2. A method according to claim 1 wherein the antibody is brought into its slit-shaped chamber between the membranes as absorbed into a porous sheet.

3. A method according to claim 1 wherein a number of vessels are contained in a cassette during the incubation and washing steps.

4. A method according to claim 3 wherein the agitation of liquid in the tank necessary during incubation and washing is produced by keeping the cassette with its contents on a swaying base.

5. A method according to claim 1 wherein in said vessel lies on its side during washing and the washing liquid can be changed by lowering and raising the liquid level in the surrounding container.

* * * * *